(12) United States Patent
Wright

(10) Patent No.: US 9,227,086 B2
(45) Date of Patent: Jan. 5, 2016

(54) HIGH ENERGY MICROBEAM RADIOSURGERY

(75) Inventor: Michael Dean Wright, Palo Alto, CA (US)

(73) Assignee: VARIAN MEDICAL SYSTEMS, INC., Palo Alto, CA (US)

(*) Notice: Subject to any disclaimer, the term of this patent is extended or adjusted under 35 U.S.C. 154(b) by 466 days.

(21) Appl. No.: 13/492,412

(22) Filed: Jun. 8, 2012

(65) Prior Publication Data

US 2013/0329857 A1 Dec. 12, 2013

(51) Int. Cl.
*A61N 5/10* (2006.01)
*H05G 1/30* (2006.01)
*G21K 5/04* (2006.01)

(52) U.S. Cl.
CPC ............ *A61N 5/1031* (2013.01); *A61N 5/1042* (2013.01); *A61N 5/10* (2013.01); *A61N 2005/1091* (2013.01); *G21K 5/04* (2013.01); *H05G 1/30* (2013.01)

(58) Field of Classification Search
CPC ........... A61N 5/00; A61N 5/10; A61N 5/103; A61N 5/1031; A61N 5/1042; A61N 5/1077; A61N 2005/00; A61N 2005/0632; A61N 2005/10; A61N 2005/103; A61N 2005/1031; A61N 5/1048; A61N 5/1092; G21K 5/00; G21K 5/04; A61B 6/00; A61B 19/00; H01J 35/00; H01J 35/02; H05G 1/00; H05G 1/08; H05G 1/26; H05G 1/30
USPC ............... 378/64, 65, 91, 101, 108, 119, 121, 378/145, 147, 149, 204, 210, 901; 600/425, 600/427, 429
See application file for complete search history.

(56) References Cited

U.S. PATENT DOCUMENTS

| | | | |
|---|---|---|---|
| 5,339,347 A * | 8/1994 | Slatkin et al. | 378/65 |
| 5,825,847 A | 10/1998 | Ruth | |
| 6,035,015 A | 3/2000 | Ruth | |
| 7,194,063 B2 | 3/2007 | Dilmanian | |
| 7,242,748 B2 | 7/2007 | Loewen | |
| 7,277,526 B2 | 10/2007 | Rifkin | |
| 7,295,653 B2 | 11/2007 | Loewen | |
| 7,301,972 B2 | 11/2007 | Loewen | |
| 8,915,833 B1 * | 12/2014 | Sahadevan | 600/1 |
| 2006/0176997 A1 * | 8/2006 | Dilmanian et al. | 378/65 |
| 2006/0178549 A1 * | 8/2006 | Dilmanian | 600/1 |
| 2008/0192892 A1 * | 8/2008 | Dilmanian et al. | 378/65 |
| 2010/0187446 A1 * | 7/2010 | Dilmanian et al. | 250/492.3 |
| 2010/0329413 A1 * | 12/2010 | Zhou et al. | 378/4 |

OTHER PUBLICATIONS

F. Avraham Dilmanian, "Interlaced X-Ray Microplanar Beams: A Radiosurgery Approach With Clinical Potential", PNAS, Jun. 20, 2006, vol. 103; 6 pages.

(Continued)

*Primary Examiner* — Anastasia Midkiff
(74) *Attorney, Agent, or Firm* — Vedder Price, P.C.

(57) ABSTRACT

A method of performing microbeam radiosurgery on a patient whereby target tissue within a patient is irradiated with high energy electromagnetic radiation via one or more microbeam envelopes with photons having respective energy magnitudes in excess of 200 keV, and maximum defined beam widths sufficiently narrow to yield a biological damage width which does not exceed a predetermined value.

11 Claims, 8 Drawing Sheets

(56) References Cited

OTHER PUBLICATIONS

F. Avraham Dilmanian, 'Tissue-Sparing Effect of X-Ray Microplanar Beams Particularly in the CNS: Is a Bystander Effect Involved?' Experimental Hematology, 2007, vol. 35; 9 pages.

K.J. Weeks et al., 'The Compton Backscattering Process and Radiotherapy', Med. Phys. Mar. 1997, vol. 24(3); 7 pages.

* cited by examiner

HIGH ENERGY MICROBEAM RADIOSURGERY

BACKGROUND

1. Field of the Invention

The present invention relates to methods for performing radiosurgery on a patient using microbeam radiation.

2. Description of the Related Art

Nearly two decades ago, a radiosurgery method was patented by Slatkin et al. (see U.S. Pat. No. 5,339,347, the disclosure of which is incorporated herein by reference). This radiosurgery method employs sub-millimeter beams of X-rays, termed microbeams. An advantageous feature of this radiosurgery technique is that the microbeams, while successfully destroying targeted diseased tissue, do not destroy the functionality of normal healthy tissue surrounding the target. Scientific studies using cell cultures and animal models show that although the normal tissue cells directly in the path of a microbeam are destroyed, the region of destruction is sufficiently small in width that the adjacent normal tissue is capable of healing the damaged region (see Dilmanian et al., *Experimental Hematology*, Vol. 35, 2007, pp. 69-77, the disclosure of which is incorporated herein by reference). Normal tissue heals when microbeams are less than 700 um in size (see Dilmanian et al., *Proceedings of the National Academy of Sciences*, Vol. 103, 2006, pp. 9709-9714, the disclosure of which is incorporated herein by reference). Diseased tissue is destroyed by cross firing from other directions, thereby creating sufficiently broad regions of damage that a healing response by adjacent tissue cannot be mounted.

Unfortunately, the great promise of microbeam radiosurgery has yet to be realized. There are two major problems. First, the only source of microbeam radiation capable of providing sufficient dose rate for radiosurgery until now has been a synchrotron. A synchrotron is a very large and expensive device. The synchrotron source which has been used for most microbeam radiosurgery studies is the European Synchrotron Radiation Facility located in Grenoble, France. The storage ring associated with this synchrotron is 300 m in diameter, and the facility cost approximately $900 M to construct. These characteristics of a synchrotron source are prohibitive.

This first problem is likely to be resolved by a new type of radiation source which utilizes the physical phenomenon of inverse Compton scattering to generate high energy X-ray photons. Such a source promises to provide the necessary dose rate, while requiring a much smaller footprint (less than 5 m in diameter) and much lower cost to construct (approximately $15 M) than a synchrotron (see Adler et al., U.S. patent application Ser. No. 13/453,338, the disclosure of which is incorporated herein by reference).

The second problem with conventional microbeam radiosurgery is the restriction of the X-ray photons comprising the microbeams to energies less than 200 keV. This restriction arises from the requirement that the dose deposition in tissue have a lateral profile (i.e., a profile in a direction orthogonal to the direction of beam propagation) with very sharp edges; that is, the lateral energy deposition in tissue must fall from the peak value abruptly (see Dilmanian et al., *Experimental Hematology*, cited above).

Referring to FIG. 1, the percentage lateral dose profile 10 in tissue required by conventional microbeam radiosurgery is shown. (Note: A percentage dose profile is obtained from a dose profile by dividing the dose at all positions by the maximum dose in the profile, and multiplying by 100.) It is preferred that the transition 14 from the peak dose value 12 to the valley dose value 16 have an 80% to 20% fall length of no more than a few tens of microns.

A percentage lateral dose profile such as shown in FIG. 1 requires incident photons of less than 200 keV because of the physical process known as Compton scattering. Compton scattering is the primary mechanism by which incident X-ray photons with energies between 100 keV and 10 MeV interact with the atoms comprising the tissues of a patient.

Referring to FIG. 2, the physical phenomenon of Compton scattering is shown. When a high energy photon 20 collides with a low energy atomic electron 22, the result is an ionized high energy electron 24 and a scattered reduced energy photon 26. Most energy deposition within the tissue of a patient is a result of secondary collisions of the high energy electron 24 with other atoms in the patient. The higher the initial energy of the electron 24, the farther the electron 24 can travel. In order to keep the width of energy deposition less than a few tens of microns within the patient, the incident X-ray photon 20 must have energy less than 200 keV.

Referring to FIG. 3, the percentage lateral dose profile associated with a 200 keV incident X-ray beam is shown. The percentage lateral flux profile 31 of the incident X-ray beam in air before striking the patient is extremely sharp, having a transition region 35 with an 80% to 20% fall length of 5 um. The associated percentage lateral dose profile 30 at a depth of 1 cm in the patient is also relatively sharp, having a transition region 34 from the peak dose value 32 to the valley dose value 36 with an 80% to 20% fall length of 25 um. (The percentage lateral dose profile 30 is obtained from Monte Carlo calculations of the Compton scattering process in water, which is a good model for the tissues of a patient.)

Referring to FIG. 4, the percentage lateral dose profile associated with a 400 keV incident X-ray beam is shown. The percentage lateral flux profile 41 of the incident X-ray beam in air before striking the patient is again very sharp, having a transition region 45 with an 80% to 20% fall length of 5 um. The associated percentage lateral dose profile 40 at a depth of 1 cm in the patient is not sharp, however, having a transition region 44 from the peak dose value 42 to the valley dose value 46 with an 80% to 20% fall length of 110 um.

Referring to FIG. 5, the percentage lateral dose profile associated with a 2 MeV incident X-ray beam is shown. The percentage lateral flux profile 51 of the incident X-ray beam in air before striking the patient is sharp, having a transition region 55 with an 80% to 20% fall length of 5 um. The associated percentage lateral dose profile 50 at a depth of 1 cm in the patient is very broad, having a transition region 54 from the peak dose value 52 to the valley dose value 56 with an 80% to 20% fall length of 275 um.

Requiring X-ray photon energies to be less than 200 keV results in insufficient dose to tissues deep within a patient. Such low energy photons are quickly absorbed by tissues near the surface of the body.

Referring to FIG. 6, the percentage dose profiles along the direction of beam propagation (i.e., in the direction of depth into the patient) for various X-ray photon energies are shown. The percentage depth dose profiles 62, 64, and 66 are those of X-ray photons of 200 keV, 400 keV, and 2 MeV, respectively. For all curves, the beam physical size is 500 um in diameter. It can be seen from FIG. 6 that the 2 MeV beam penetrates much deeper into a patient than the 200 keV and 400 keV beams. In general, the higher the photon energy, the deeper the beam penetrates into a patient.

SUMMARY

In accordance with the presently claimed invention, a method of performing microbeam radiosurgery on a patient provides for irradiating target tissue within a patient with high energy electromagnetic radiation via one or more microbeam envelopes with photons having respective energy magnitudes in excess of 200 keV, and maximum defined beam widths sufficiently narrow to yield a biological damage width which does not exceed a predetermined value.

DETAILED DESCRIPTION

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

Figure 1:
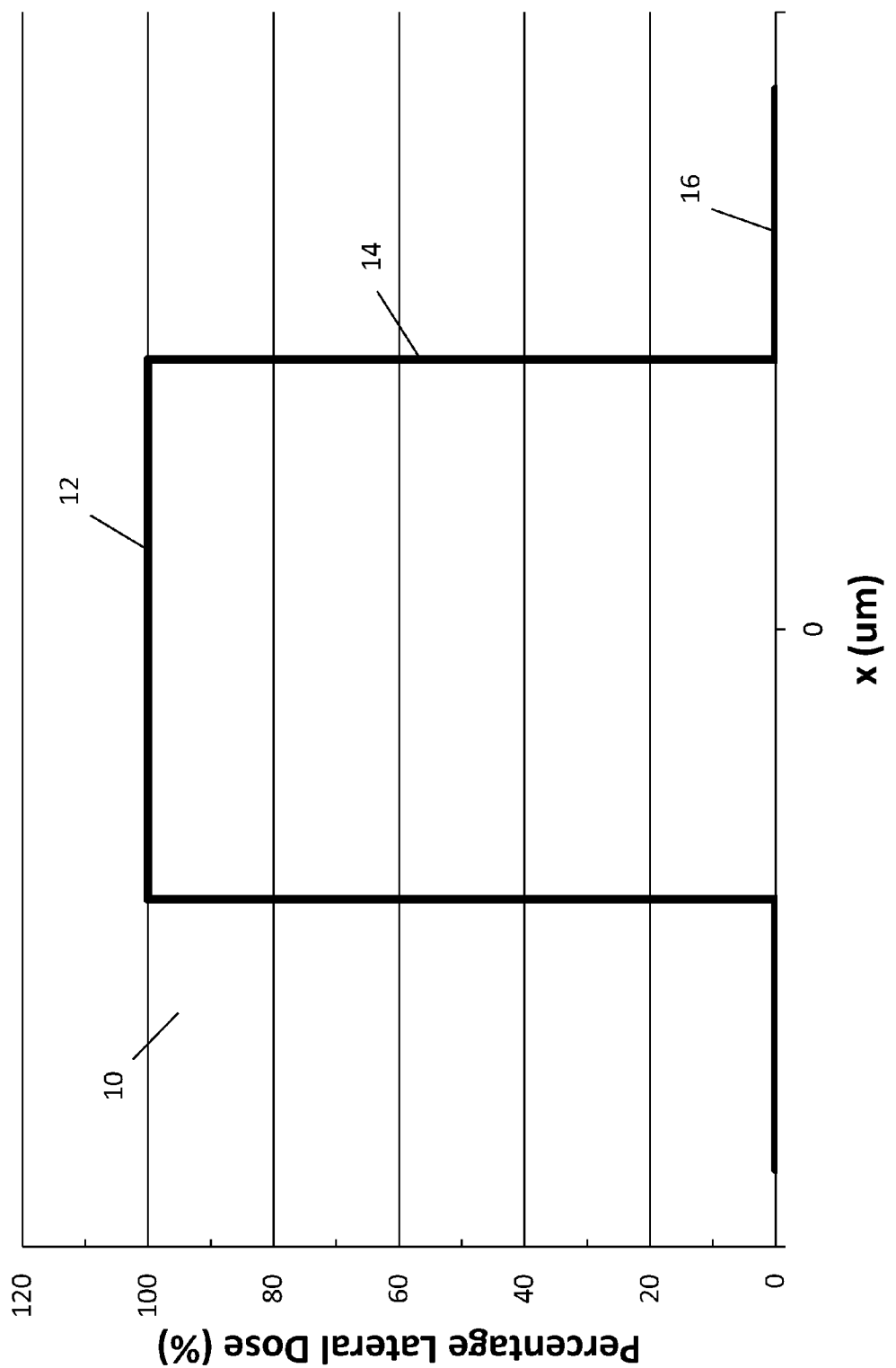
FIG. 1 depicts a percentage lateral dose profile.
Figure 2:
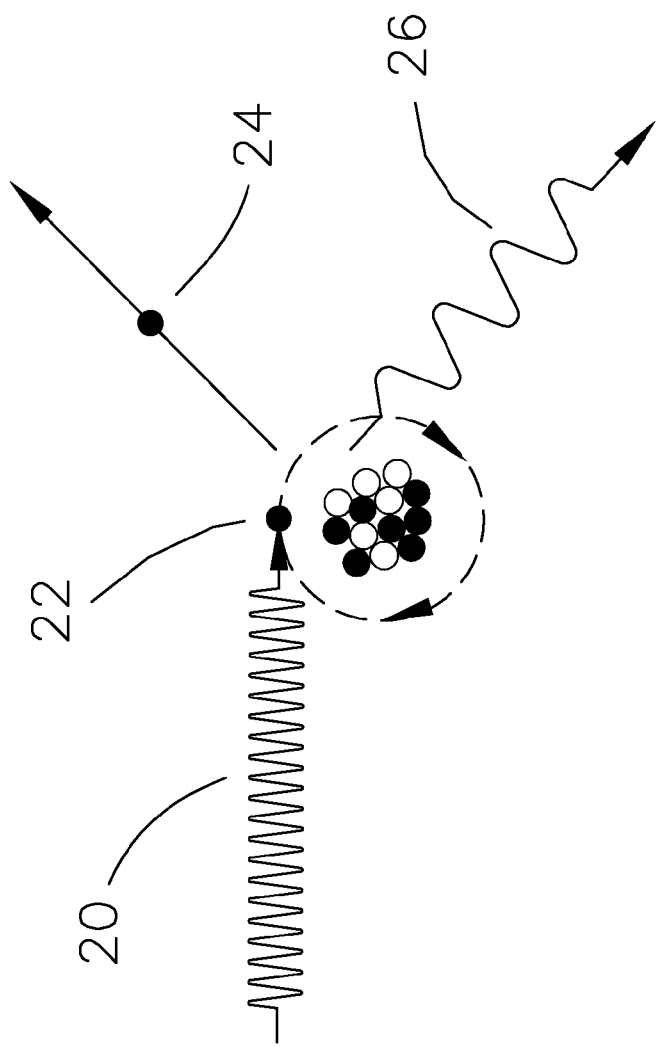
FIG. 2 depicts the physical phenomenon of Compton scattering.
Figure 3:
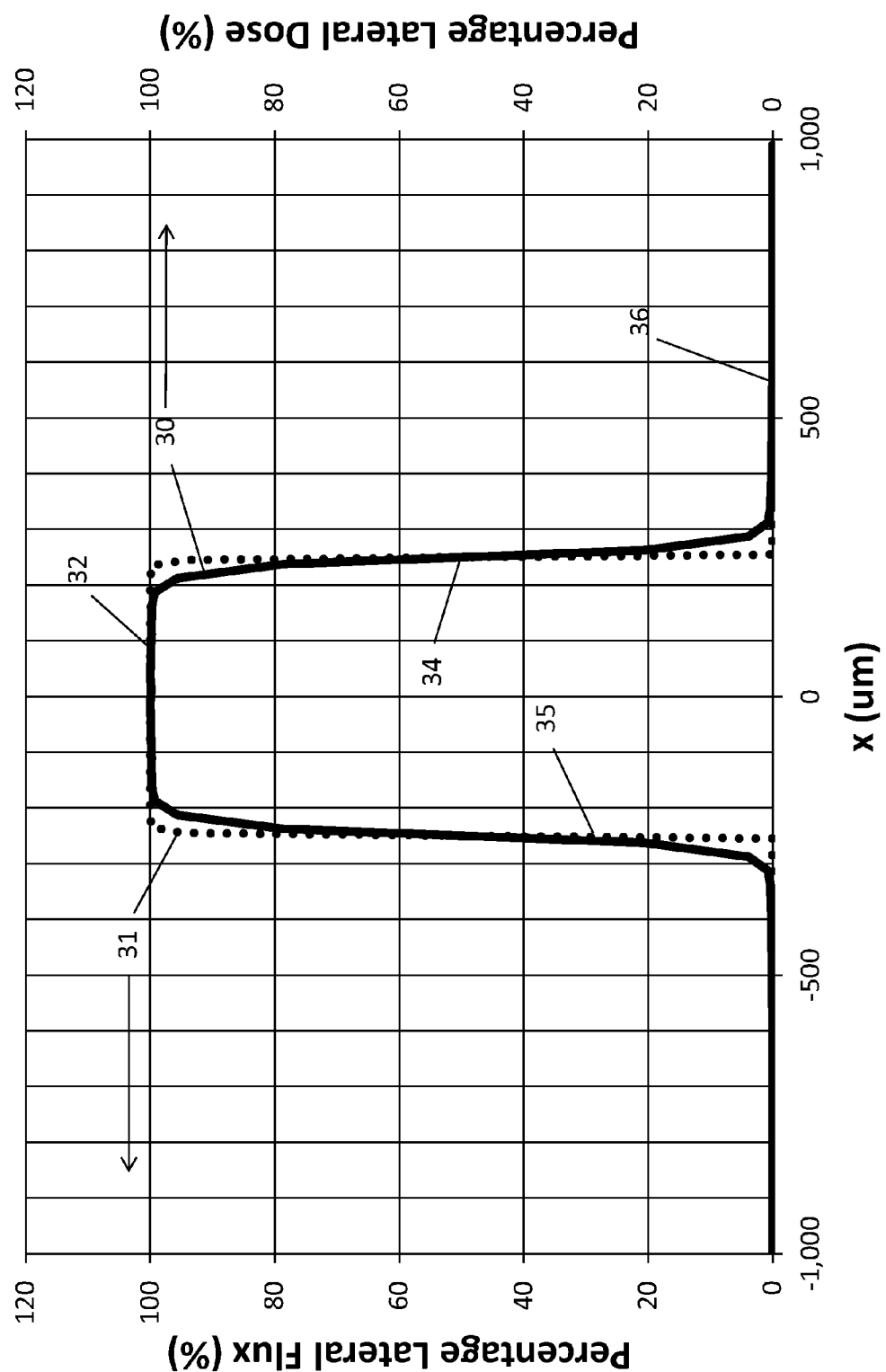
FIG. 3 depicts a percentage lateral dose profile associated with a 200 keV incident X-ray beam.
Figure 4:
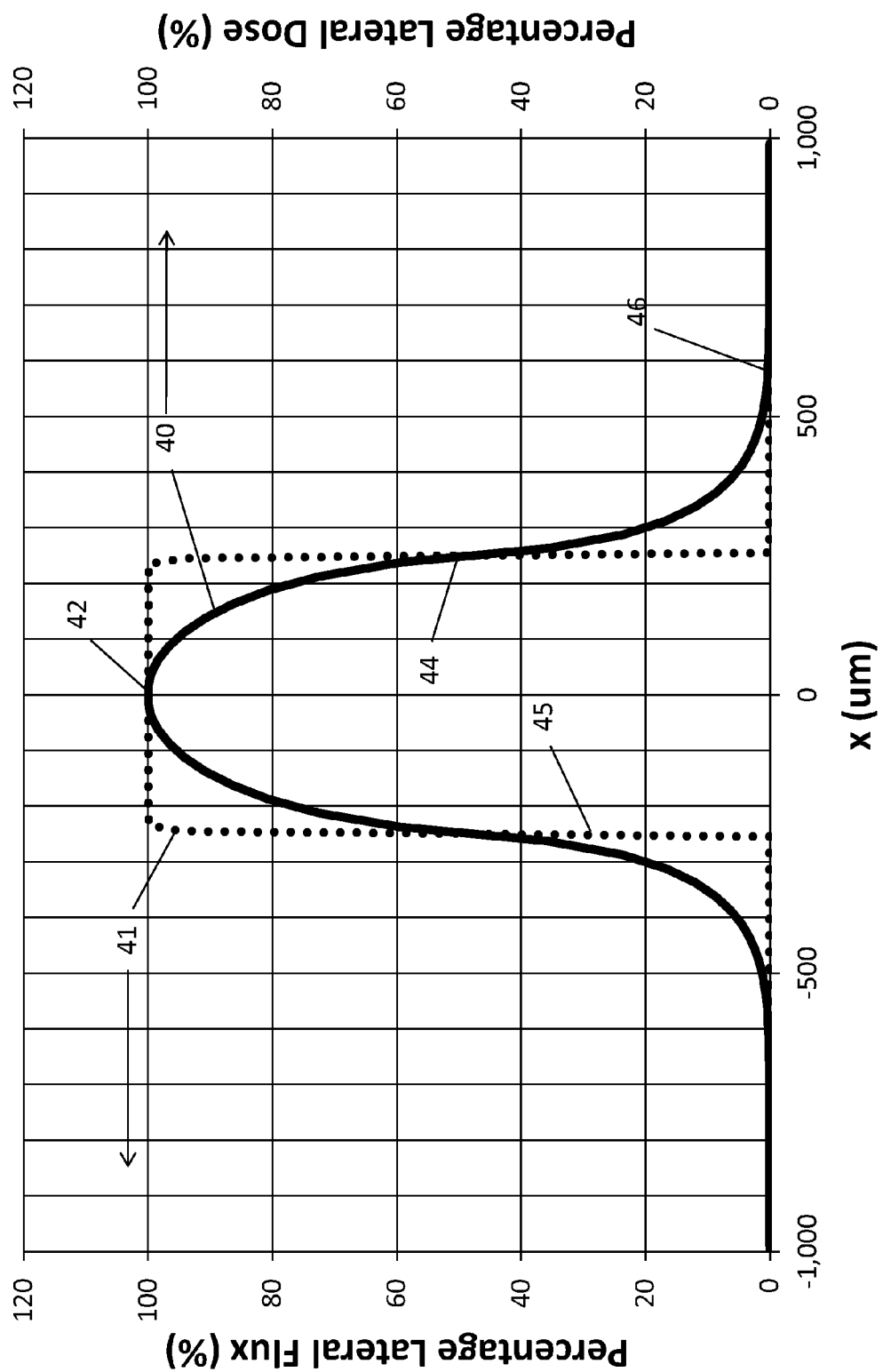
FIG. 4 depicts a percentage lateral dose profile associated with a 400 keV incident X-ray beam.
Figure 5:
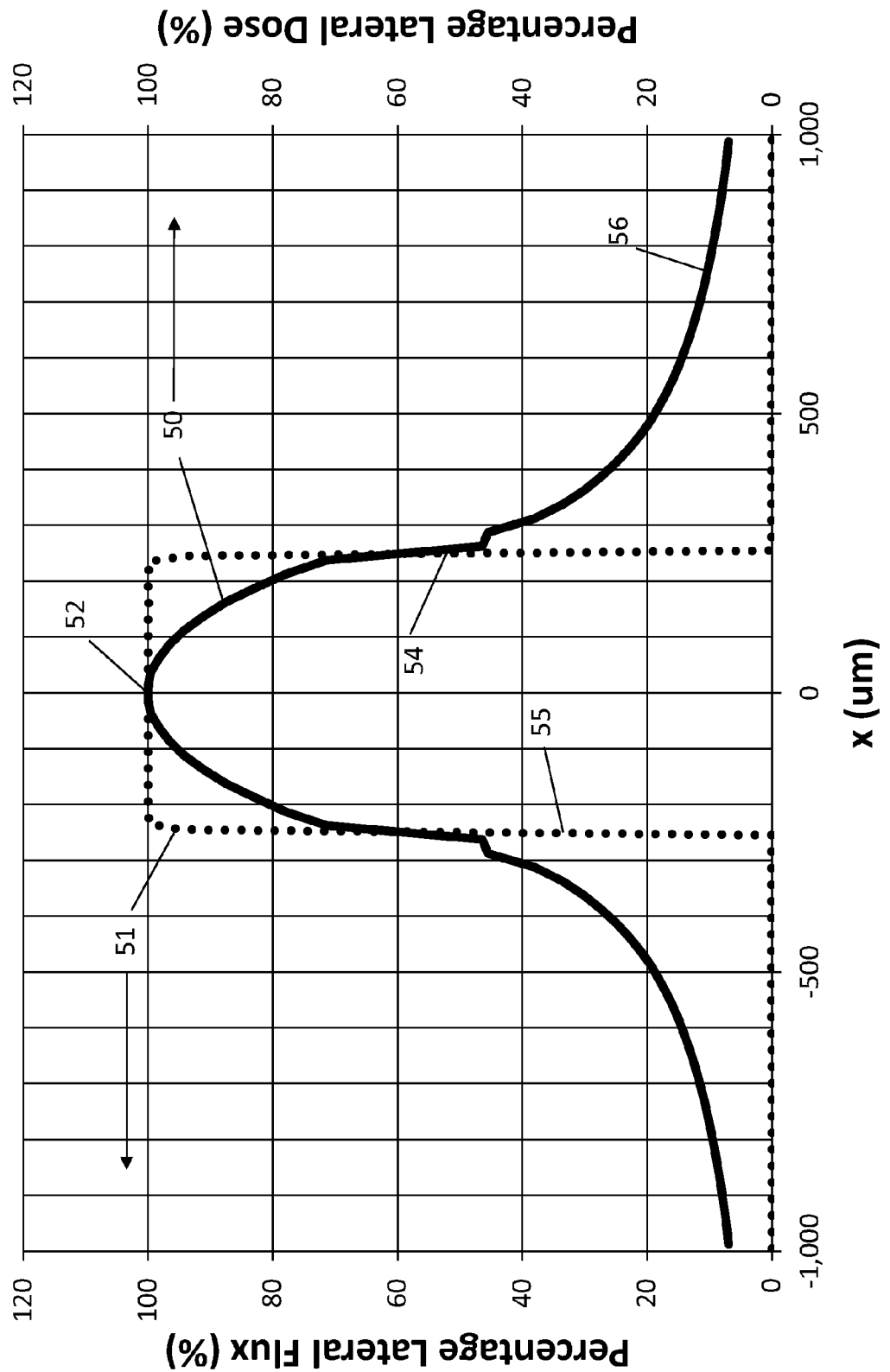
FIG. 5 depicts a percentage lateral dose profile associated with a 2 MeV incident X-ray beam.
Figure 6:
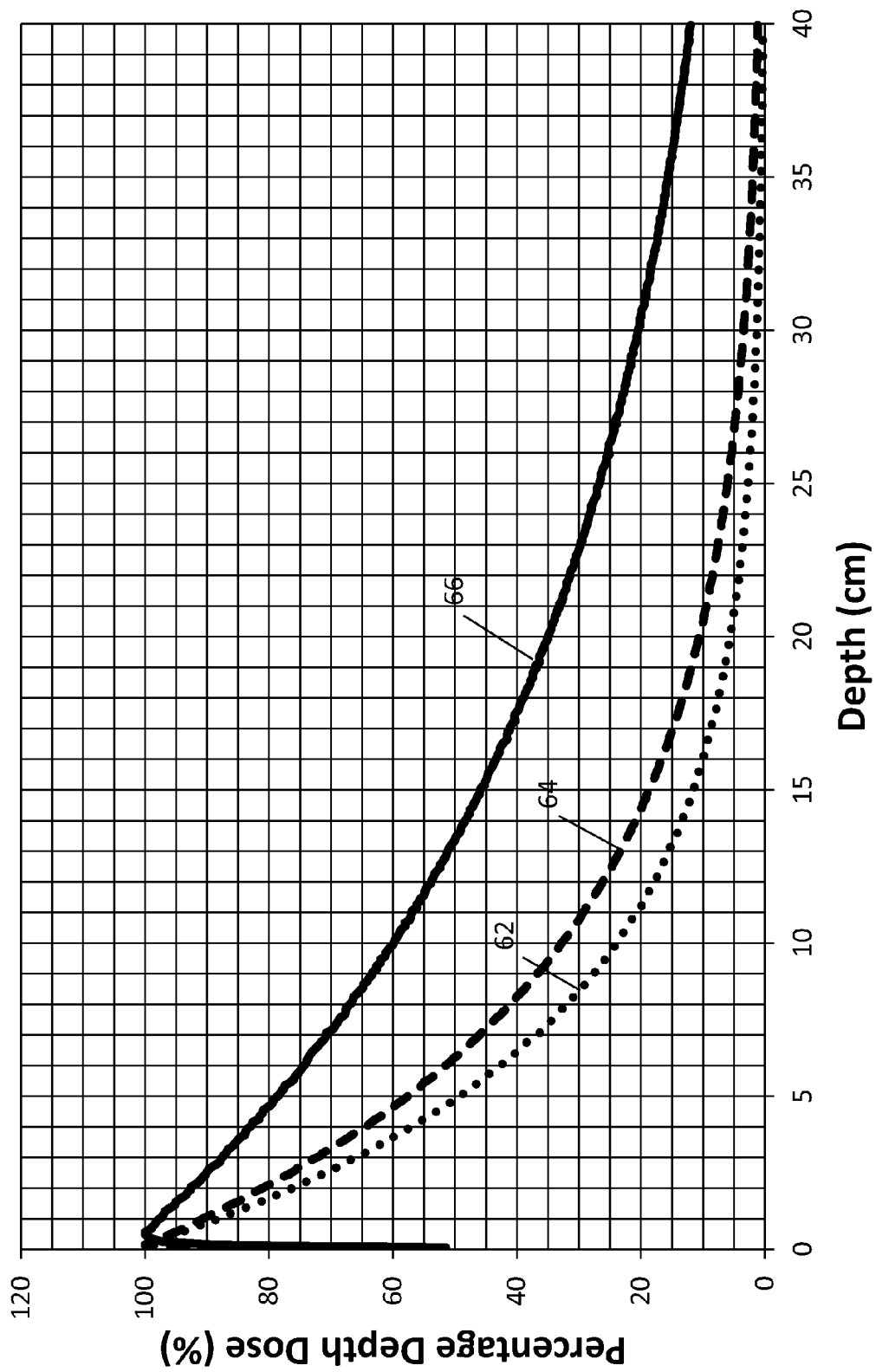
FIG. 6 depicts percentage depth dose profiles for various X-ray photon energies.
Figure 7:
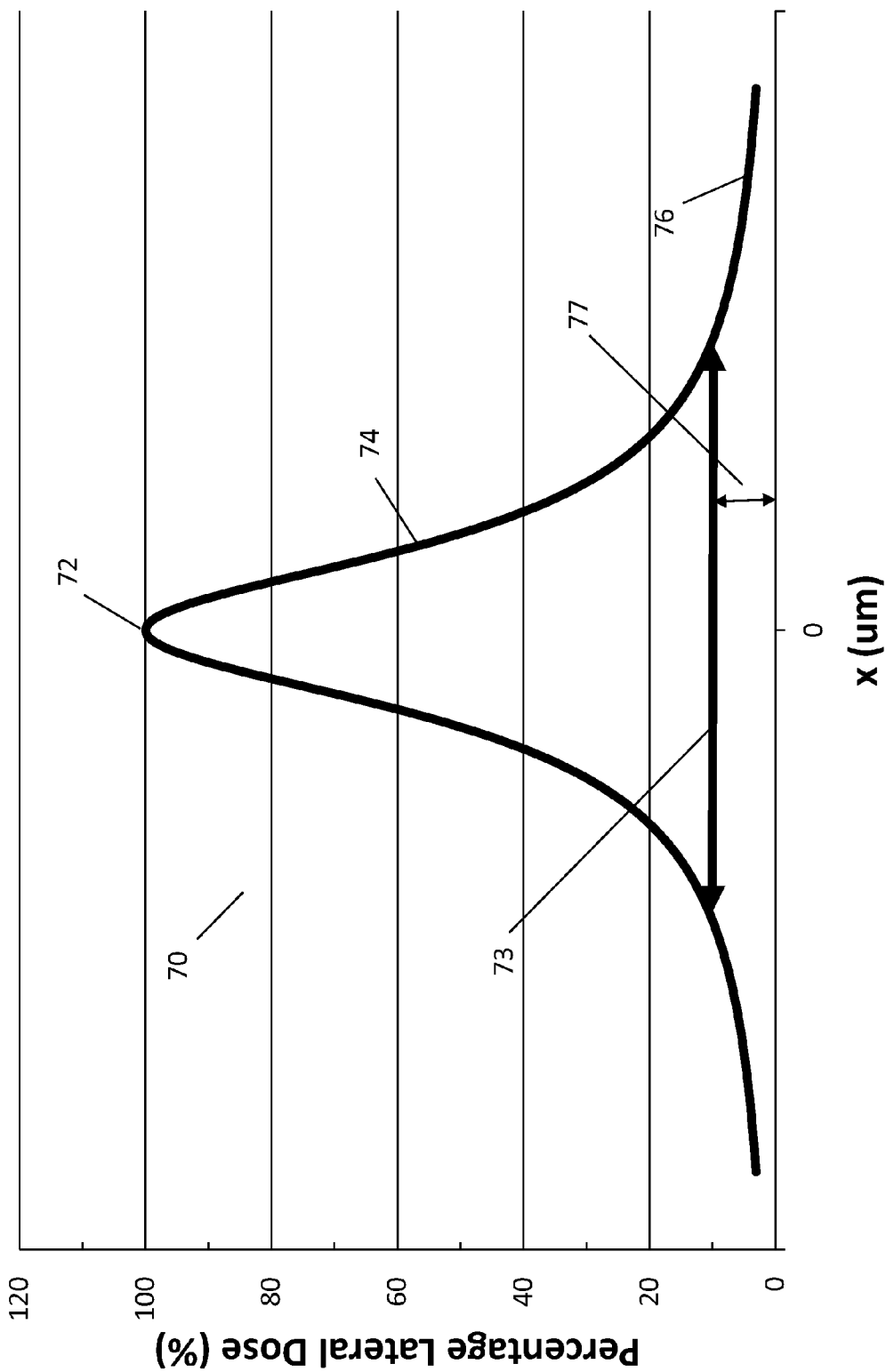
FIG. 7 depicts the concepts of graded percentage lateral dose profile and biological damage width.

Referring to FIG. 7, the concepts of graded percentage lateral dose profile and biological damage width are shown. For a graded percentage lateral dose profile 70, the transition 74 from the peak dose 72 to the valley dose 76 is not abrupt. The 80% to 20% fall length may be as large as a few hundred microns. The width of the percentage lateral dose profile 73 above a threshold value 77 is defined as the biological damage width. For doses above the threshold value 77, significant damage is done to tissue. The requirements for a graded percentage lateral dose profile are twofold. First, the peak dose 72 must be sufficiently larger than the threshold dose 77 to destroy target tissue. It is anticipated that a peak-to-threshold dose ratio ($D_{72}/D_{77}$) greater than or equal to 10 is preferred. Second, the biological damage width 73 is preferably less than or equal to 700 um, which is the maximum damage width that can be healed by surrounding normal tissue.

To achieve a biological damage width less than or equal to 700 um for X-ray photon energies above 200 keV, the width of the incident X-ray beam is made considerably smaller than 700 um. The width of the incident X-ray beam is made sufficiently small that, upon accounting for the Compton scattering process, the biological damage width is within the desired range.

Figure 8:
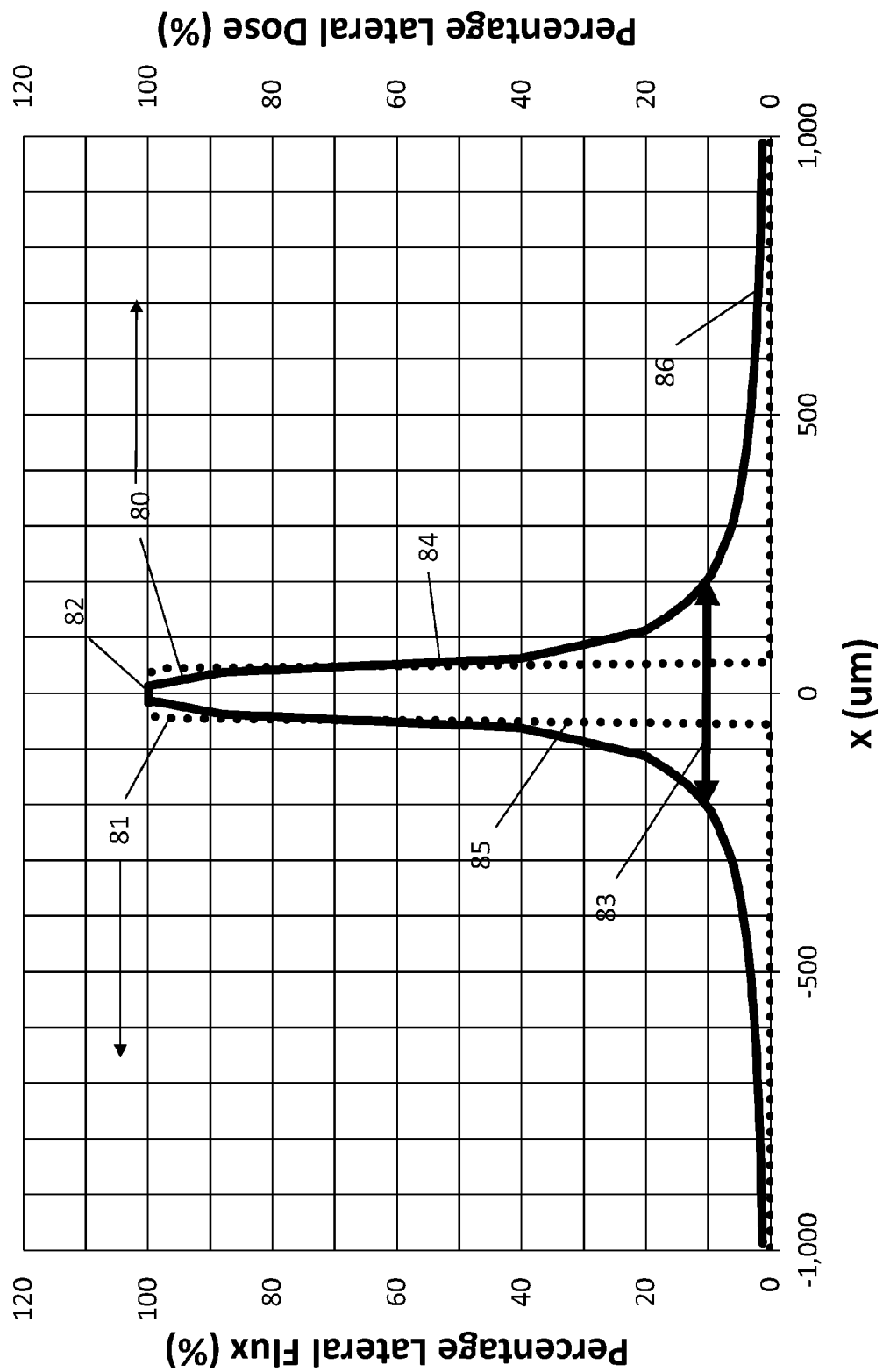
FIG. 8 depicts a graded percentage lateral dose profile associated with a 100 um wide incident 2 MeV X-ray beam.

Referring to FIG. 8, the graded percentage lateral dose profile associated with a 100 um wide incident 2 MeV X-ray beam is shown. The percentage lateral flux profile 81 of the incident X-ray beam in air before striking the patient is extremely sharp, having a transition region 85 with an 80% to 20% fall length of 5 um. The associated graded percentage lateral dose profile 80 at a depth of 1 cm in the patient has a transition region 84 from the peak dose value 82 to the valley dose value 86 with an 80% to 20% fall length of 70 um. For a peak-to-threshold dose ratio of 10, the biological damage width 83 is 400 um in width.

In accordance with a preferred embodiment, target tissue in a patient is irradiated with X-ray microbeams from one or more directions. For any given direction, one or more X-ray microbeams are used. Each X-ray microbeam has a maximum defined beam width sufficiently narrow to yield a biological damage width not exceeding a predetermined value. For the case of irradiation with multiple X-ray microbeams from a given direction, the microbeams are substantially mutually parallel and are mutually separated by a minimum defined inter-beam spacing to provide an undamaged tissue width sufficient to promote healing of damaged non-target tissue.

Various other modifications and alternatives in the structure and method of operation of this invention will be apparent to those skilled in the art without departing from the scope and the spirit of the invention. Although the invention has been described in connection with specific preferred embodiments, it should be understood that the invention as claimed should not be unduly limited to such specific embodiments. It is intended that the following claims define the scope of the present invention and that structures and methods within the scope of these claims and their equivalents be covered thereby.

What is claimed is:

1. A method of performing high energy microbeam radiosurgery on a patient, comprising:
irradiating a target tissue, within a patient, with high energy electromagnetic radiation via one or more microbeam envelopes which are mutually spatially distinct and each of which has a respective maximum defined beam width, wherein
said high energy electromagnetic radiation includes photons having respective energy magnitudes within a spectrum with a peak value in excess of 200 keV,
said peak value and said maximum defined beam width yield a graded lateral dose profile having a peak dose and non-abrupt transitions to first and second valley doses, and
each of said one or more microbeam envelopes yields a biological damage width defined by a width of said graded lateral dose profile above a threshold dose value which is between said peak and valley doses and above which biological damage occurs.

2. The method of claim 1, wherein tissue adjacent each of said one or more microbeam envelopes supports recovery of non-target tissue.

3. The method of claim 1, wherein said one or more microbeam envelopes comprises a plurality of microbeam envelopes which are mutually spatially distinct.

4. The method of claim 3, wherein adjacent ones of said plurality of microbeam envelopes are mutually separated by a minimum defined inter-beam spacing to provide an undamaged tissue width which is sufficient to promote healing of damaged non-target tissue.

5. The method of claim 3, wherein other tissue between adjacent ones of said plurality of microbeam envelopes supports recovery of non-target tissue.

6. The method of claim 3, wherein said plurality of microbeam envelopes have substantially equal beam widths.

7. The method of claim 3, wherein adjacent ones of said plurality of microbeam envelopes are mutually separated by a minimum defined inter-beam spacing substantially greater than said maximum defined beam width.

8. The method of claim 3, wherein:
adjacent ones of said microbeam envelopes are mutually separated by a minimum defined inter-beam spacing; and
a ratio of said minimum defined inter-beam spacing to said maximum defined beam width is greater than or equal to two.

9. The method of claim 3, wherein said plurality of microbeam envelopes comprises a plurality of substantially mutually parallel microbeam envelopes.

10. The method of claim 1, wherein a ratio of said peak dose value to said threshold dose value is greater than or equal to 10.

11. The method of claim 1, wherein said width of said graded lateral dose profile at said threshold dose value is less than or equal to 700 microns.

* * * * *